(12) United States Patent
Mochizuki (10) Patent No.: US 7,767,451 B2
(45) Date of Patent: Aug. 3, 2010

(54) FELINE CELL CAPABLE OF BEING CULTURED WITHOUT ANIMAL-DERIVED PROTEIN, AND METHOD FOR PRODUCING VIRUS AND METHOD FOR PRODUCING VACCINE USING THEREOF

(75) Inventor: Masami Mochizuki, Yokohama (JP)

(73) Assignee: Kyoritsu Seiyaku Corporation, Tokyo (JP)

( * ) Notice: Subject to any disclaimer, the term of this patent is extended or adjusted under 35 U.S.C. 154(b) by 0 days.

(21) Appl. No.: 12/226,748

(22) PCT Filed: Apr. 28, 2006

(86) PCT No.: PCT/JP2006/309045

§ 371 (c)(1),
(2), (4) Date: Dec. 5, 2008

(87) PCT Pub. No.: WO2007/125605

PCT Pub. Date: Nov. 8, 2007

(65) Prior Publication Data

US 2009/0098159 A1    Apr. 16, 2009

(51) Int. Cl.
*C12N 15/16*    (2006.01)
*A61K 39/215*    (2006.01)

(52) U.S. Cl. ................ 435/351; 435/350; 435/243; 424/221.1

(58) Field of Classification Search .......... 435/351; 424/233.1
See application file for complete search history.

(56) References Cited

FOREIGN PATENT DOCUMENTS

| JP | 2002-520014 | 7/2002 |
|---|---|---|
| JP | 2005-532057 | 10/2005 |
| WO | WO 03/002713 A2 | 1/2003 |
| WO | WO 2004/005493 A1 | 1/2004 |

OTHER PUBLICATIONS

Schekli et al. J. Virol. 1997, vol. 71, No. 12, pp. 9499-9507.*
Holmes et al. Virology 2004, vol. 324, pp. 510-524.*
Compton et al. J. Virol. 1992, vol. 66, No. 12, pp. 7420-7428.*
Kai et al. Jpn. J. Vet. Sci. 1988, vol. 50, No. 1, pp. 247-249.*
Mochizuki (B) Vaccine, 2006, vol. 24, pp. 1744-1748.*
Masami Mochizuki et al., *Antigenic and Plaque Variations of Serotype II Feline Infectious Peritonitis Coronaviruses*, 59 J. Vet. Med. Sci. 253 (1997).
B Makoschey et al., *Serum-free Produced Bovine Herpesvirus Type 1 and Bovine Parainfluenza Type 3 Virus Vaccines are Efficacious and Safe*, 39 Cytotechnology 139 (2002).
S. J. Froud, *The Development, Benefits and Disadvantages of Serum-Free Media*, 99 Dev. Biol. Stand. 157 (1999).
O. W. Merten, *Safety Issues of Animal Products Used in Serum-Free Media*, 99 Dev. Biol. Stand. 167 (1999).
O. W. Merten, *Development of Serum-Free media for Cell Growth and Production of Viruses/Viral Vaccines—Safety Issues in Animal Products Used in Serum-Free Media*, 111 Dev. Biol. Stand. 233 (2002).
Noe et al., *Fed-Batch Strategies for Mammalian Cell Cultures*, in Animal Cell Technology: Products of Today, Prospects for Tommorrow 413 (Spier et al. eds., 1994).
S. M. Kwon et al., *Use of Plant-Derived Protein Hydrolysates for Enhancing Growth of Bombyx mori (silkworm) Insect Cells in Suspension Culture*, 42 Biotechnol. Appl. Biochem. 1 (2005).
B. H. Chun et al., *Use of Plant Hydrolysates for Varicella Virus Production in Serum-Free Medium*, 27 Biotechnol. Letters 243 (2005).
Pedersen et al., *Infection Studies in Kittens, Using Feline Infectious Peritonitis Virus Propogated in Cell Culture*, 42 Am. J. Vet. Res. 363 (1981).

* cited by examiner

*Primary Examiner*—Zachariah Lucas
*Assistant Examiner*—Bao Qun Li
(74) *Attorney, Agent, or Firm*—The Nath Law Group; Joshua B. Goldberg; Ari G. Zytcer (57) ABSTRACT

The present invention provides a cell strain which is derived from an fcwf-4 cell that is a cell derived from a feline whole fetus and which is capable of being cultured without animal-derived proteins, a method for producing the cell strain, and a method for producing a virus by using the cell. An inexpensive and safe feline vaccine can be produced according to the present invention.

6 Claims, 5 Drawing Sheets

Growth Curves of Feline Herpes Virus-1, C7301 Strain

FIG. 4

Growth Curves of Feline Calicivirus F9 Strain

Growth Curves of Feline Infectious Peritonitis Virus, M91-267 Strain

FIG. 9

Growth Curves of Feline Panleukopenia Virus, TU-1 Strain

FELINE CELL CAPABLE OF BEING CULTURED WITHOUT ANIMAL-DERIVED PROTEIN, AND METHOD FOR PRODUCING VIRUS AND METHOD FOR PRODUCING VACCINE USING THEREOF

TECHNICAL FIELD

The present invention relates to a feline cell strain capable of being cultured without proteins derived from animals and a method for producing the same. The present invention also relates to a method for producing a virus using the cell strain, a method for producing a diagnostic antigen, a method for producing a vaccine, and a diagnostic test method. Further, the present invention relates to a medium used for culturing the cell strain.

BACKGROUND ART

A half-century or more has passed since the creation of a technique of culturing animal cells and the like in a test tube. Such a technique has been significantly developed together with the progress of science and technology.

In general, when a living animal is directly used for experiments, the results can be easily understood. However, such direct examination of a living animal has been problematic both technically and economically. Thus, a portion has been excised from an animal, and the cells thereof have been proliferated in an artificial environment such as in a Petri dish or in a test tube. This method is called a tissue culture method or a cell culture method. Since such a technique has not been difficult, it has become possible to produce pharmaceuticals, vaccines, diagnostic antigens, etc., by this method. For culturing animal cells in vitro, however, it is required to culture the cells almost under the same conditions as the original in vivo conditions. For example, conditions, such as an aseptic state or a temperature environment that is set at the same temperature as that in a living body, are applied.

Further, even if the aforementioned conditions have been satisfied, it has been necessary for cell division and proliferation to additionally supply a "cell growth factor" as a nutrient. Examples of such a cell growth factor include various types of hormones, insulin, putrescine, and a fibroblast growth factor. However, such cell growth factors have not yet been clarified in all cell species.

Accordingly, animal serums whose effect can be nonspecifically expected and which contain many "unknown" components are used instead of cell growth factors. Among such animal serums, bovine serum is selected because of a large bovine population and also because it can be stably supplied. Fetal calf serum has been frequently used because it contains only a small amount of toxic protein. In scientific studies, there are cases where a bovine-derived protein may be contained in a test material, although bovine is not an animal species of interest. However, the use of such a bovine-derived protein as a pharmaceutical for a human or other animal species may cause a problem.

The first problem is related to allergy. When a vaccine or a drug that contains bovine serum is parenterally injected into humans or non-bovine animals, a first injection may not cause a problem in many cases. However, a second injection or later injections may cause a problem regarding an allergy reaction. This phenomenon can be immunologically explained. That is, an animal only slightly reacts with a high-molecular substance (e.g. a protein having a molecular weight of 10,000 daltons or more) when the substance is exposed to the animal for the first time, and thus the administered substance is decomposed in vivo. However, a memory regarding exposure remains in immune system. Accordingly, when the same substance (antigen) is exposed to the animal for the second time or later, immunocytes that memorize the first exposure directly react with the substance, and as a result, a vital reaction that is stronger than that of the first exposure occurs in a short time. Depending on the types of humans or animals, there may be cases where they may have an unfavorable reaction with an antigen that is exposed from the outside. Such a reaction is typically referred to as an allergy reaction. Such an allergy reaction causes fever or swelling at an injected site, and in the worst case, humans or animals die from dyspnea due to respiratory obstruction and collapse.

The second problem is related to the contamination of pathogens or bovine serum antibodies contained in bovine serum. A famous example is contamination with Pestivirus, Retrovirus, Mycoplasma, etc. of bovine origin. Recently, prion that is a pathogen of bovine spongiform encephalopathy (BSE) known as mad cow disease has become problematic.

As stated above, although the use of bovine serum may cause troublesome occurrences, such bovine serum has commonly been used all over the world for production of vaccines particularly for use in a veterinary field that targets animals.

However, an attempt not to use bovine serum in the cell culture method (a serum-free medium (SFM) and a serum-free cell culture method) and the production of an experimental vaccine for bovines using such a serum-free medium and such a serum-free cell culture method have currently been reported (Makoschey et al., Serum-free produced bovine herpesvirus type 1 and bovine parainfluenza type 3 virus vaccines are efficacious and safe. Cytotechnology, 39: 139-145, 2002). In place of growth of cells in a cell culture medium from which serum components were removed, growth of cells in an existing medium, or a newly devised medium, to which various hormones and cell growth factors were added is disclosed in the following literatures:

Froud, S. J. The development, benefits and disadvantages of serum-free media. Brown, F., Cartwright, T., Horaud, F., Spieser, J. M. (eds): Animal sera, animal sera derivatives and substitutes used in the manufacture of pharmaceuticals; Viral safety and regulatory aspects. Dev. Biol. Stand., Basel, Karger, 1999, vol. 99, pp 157-166;

Merten, O.-W. Safety issues of animal products used in serum-freemedia. Brown, F., Cartwright, T., Horaud, F., Spieser, J. M. (eds): Animal sera, anima sera derivatives and substitutes used in the manufacture of pharmaceuticals: Viral safety and regulatory aspects. Dev. Biol. Stand., Basel, Karger, 1999, vol. 99, pp 167-180; and Merten, O.-W. Development of serum-free media for cell growth and production of viruses/viral vaccines—Safety issues of animal products used in serum-free media. Brown, F., Hendriksen, C., Sesardic, D., Cussler, K. (eds): Advancing science and elimination of the use of laboratory animals for development and control of vaccines and hormones. Dev. Biol. Stand., Basel, Karger, 2002, vol. 111, pp 233-257.

Further, use of plant-derived components as medium additives is disclosed in the following literatures.

Noe et al., Fed-batch strategies for mammalian cell cultures. In, Spier, R. E., Griffiths, J. B., Berthold, W. (eds) Animal Cell Technology: products of Today, prospects for tomorrow, Oxford, Butterworth-Heinemann, 1994, pp 413-418.

Kazushi Shibuya et al.: Serum-free medium for animal cell culture, Published Japanese translation of PCT international publication for patent application (A), Japanese Patent Application Publication No. P2002-520014A (publication date:

Jul. 9, 2002). This literature discloses that Chinese hamster ovary cells are cultured in a medium prepared by adding soybean protein hydrolysates, a yeast extract and optionally wheat protein hydrolysates to a uniquely prepared medium. As the soybean protein hydrolysates, various hydrolysates such as soluble polypeptides obtained by partial hydrolysis with a digestive enzyme are disclosed.

Kwon, S. M. et al. Use of plant-derived protein hydrolysates for enhancing growth of *Bombyx mori* (silkworm) insect cells in suspension culture. Biotechnol. Appl. Biochem., 42: 1-7, 2005. This literature discloses that plant-derived protein hydrolysates (trade name: HyPep 1510; Difco Co., Detroit, Mich., USA) can be used as a substitute for conventional bovine serum inculturing silkworm-derived insect cells, but does not disclose the composition of a medium used therein.

Chun, B.-H. et al. Use of plant hydrolysates for varicella virus production in serum-free medium. Biotechnol. Letters 27: 243-248, 2005. This literature discloses that human fetal lung cells (MRC-5) are cultured in a medium prepared by adding soybean protein hydrolysates etc., but not bovine serum, to a 2:1 mixture of Dulbecco's modified Eagle medium (DMEM) and Nutrient Mixture (Ham's F-12), and also that in this cell culture system, chickenpox virus is cultured. However, the medium used therein is compounded with recombinant human insulin, a recombinant human epidermal growth factor and a recombinant human fibroblast growth factor and contains animal proteins.

An animal protein-free medium for culturing cells (Baxter International Incorporated, Japanese Patent Application Publication No. P2005-532057A). This literature discloses a method of culturing cells by using a non-animal peptides derived from soybean hydrolysates and yeast hydrolysates, wherein the cells are cat-derived CRFK cells. However, the composition of a medium used therein is not disclosed.

As described above, a cat-derived cell strain produced without using animal-derived proteins, a medium used for culturing the same, and a method of multiplying a virus for use in feline vaccines, have not been disclosed. Further, a virus that infects cats will hardly multiply in other animal species without exception, and thus even if cells derived from other animals can be cultured without animal-derived proteins, such a technique cannot be applied to cat-derived cells.

Accordingly, there has been demand for cat-derived cells cultured in a medium not containing animal-derived proteins, an animal-derived protein-free medium for culturing the cells, safe vaccines and examination reagents for cats.

DISCLOSURE OF INVENTION

One aspect of the invention relates to a cell strain which is derived from an fcwf-4 cell that is a cell derived from a feline whole fetus and which is capable of being cultured without animal-derived proteins. This cell strain may be an internationally deposited cell strain or a cell strain having biological properties equivalent to those of the cell strain.

One aspect of the invention relates to a method for producing a cell strain, which comprises adapting an fcwf-4 cell to a serum- and cell growth factor-containing culture medium, and culturing the cell in an animal-derived protein-free medium containing a plurality of soybean-derived peptones in a 1:1 mixture of a Dulbecco's modified Eagle medium and Nutrient Mixture (Ham's F-12), to produce a cell strain capable of being cultured without animal-derived proteins. The soybean-derived peptone is preferably a combination of soybean peptone (Peptone from soybean, enzymatic digest, Catalogue No. 87972, manufactured by Fluka) and Polypeptone S (POLYPEPTON-S, Catalogue No. 391-00125, manufactured by Nihon Pharmaceutical Co., Ltd.).

One aspect of the invention relates to a method for cultivating a virus, which comprises infecting a cell strain with a virus, and culturing the infected cell strain to multiply the virus. The medium in culturing the infected cell strain may be an animal-derived protein-free medium containing a plurality of soybean-derived peptones in a 1:1 mixture of a Dulbecco's modified Eagle medium and Nutrient Mixture (Ham's F-12). The soybean-derived peptones are preferably a combination of soybean peptone (Peptone from soybean, enzymatic digest, Catalogue No. 87972, manufactured by Fluka) and Polypeptone S (POLYPEPTON-S, Catalogue No. 391-00125, manufactured by Nihon Pharmaceutical Co., Ltd.). A suspension culture method may be used in culturing the infected cell strain. The virus may be a virus selected from the viral group consisting of Coronaviridae, Caliciviridae, Herpesviridae and Parvoviridae. The virus may be a virus selected from feline calicivirus, feline herpesvirus-1 (feline viral rhinotracheitis virus), feline parvovirus, feline panleukopenia virus, canine parvovirus type 2, feline coronavirus, feline enteric coronavirus, feline infectious peritonitis virus, canine coronavirus, canine respiratory coronavirus, transmissible gastroenteritis virus of swine, porcine epidemic diarrhea virus, and bovine coronavirus.

One aspect of the invention relates to a method for producing a diagnostic antigen, which comprises using a virus produced by the method described above.

One aspect of the invention relates to a method for producing a vaccine, which comprises using a virus produced by the method described above.

One aspect of the invention relates to a diagnostic test method which comprises using a virus or a viral antigen produced by the method described above.

One aspect of the invention relates to an animal-derived protein-free medium comprising plural soybean-derived peptones in a 1:1 mixture of a Dulbecco's modified Eagle medium and Nutrient Mixture (Ham's F-12). The soybean-derived peptones are preferably a combination of soybean peptone (Peptone from soybean, enzymatic digest, Catalogue No. 87972, manufactured by Fluka) and Polypeptone S (POLYPEPTON-S, Catalogue No. 391-00125, manufactured by Nihon Pharmaceutical Co., Ltd.).

According to one aspect of the present invention, the cell strain derived from an fcwf-4 cell is cultured without animal-derived proteins, so that when a virus produced by using the cell strain is used as a vaccine and examination reagent, a safe vaccine and examination reagent can be provided.

According to one aspect of the invention, a virus can be multiplied by using an inexpensive commercial medium, so that when a virus produced by using the medium is used as a vaccine and examination reagent, an inexpensive vaccine and examination reagent can be provided.

According to one aspect of the invention, the medium does not contain animal-derived proteins, so that when virus-infected cells are cultured in this medium, a safe vaccine and examination reagent can be provided.

In this specification, the phrases "does not contain animal-derived proteins" and "animal-derived protein-free" mean that animal-derived protein components that can particularly cause allergy are not contained. The proteins that can cause allergy include, for example, animal-derived serum and its portion i.e. serum albumin, animal proteins such as cell growth factors, and a wide variety of animal-derived additives (Bacto Peptone, Tryptose Phosphate Broth, etc.).

BEST MODE FOR CARRYING OUT THE INVENTION

For development of safe and effective vaccines that can be used in cats, an fcwf-4 cell that is a feline whole fetus-derived cell having a wider virus infection spectrum was selected. The fcwf-4 cell is a feline fetus-derived "macrophage" cell that is a cell strain created in 1979 by Niels C. Pedersen in Department of veterinary Medicine, University of California (Pedersen, N. C., J. F. Boyle, and K. Floyd. 1981. Infection studies in kittens, using feline infectious peritonitis virus propagated in cell culture. Am. J. Vet. Res. 42: 353-367). The fcwf-4 cell has been registered with ATCC (American Type Culture Collection) by the creator himself (No. CRL-2787).

In an animal-derived protein-free commercial basal medium (for example, Eagle's MEM, RPMI 1640 Medium, McCoy's 5A Medium, Leiovitz's L-15Medium, Dulbecco's modified Eagle medium (DMEM), and Nutrient Mixture (Ham's F-12)), fcwf-4 cells do not grow unless bovine serum is added to the medium. Accordingly, fcwf-4 cells need to be adapted and subcultured serially.

For adaptation of fcwf-4 cells, the cells can be cultured first in a fetal bovine serum-containing medium while the concentration of fetal bovine serum is gradually decreased. The medium that may be used includes, but is not limited to, a commercial medium "VP-SFM" (Catalogue No. 11681-020, manufactured by Invitrogen) containing 10 ng/ml recombinant epidermal growth factor. The concentration of fetal bovine serum may be changed from 0.25% to 0.1% and further to 0.05%.

Then, the cells can be adapted to a medium prepared by adding soybean-derived peptone to a serum-free medium. The serum-free medium that may be used includes, but is not limited to, a mixed medium consisting of a DMEM medium (Catalogue No. 11885-084, manufactured by Invitrogen) and Nutrient Mixture (Ham's F-12, Catalogue No. 11765-054, manufactured by Invitrogen). Examples of the soybean-derived peptone include, but are not limited to, soybean peptone (Peptone from soybean, enzymatic digest, Catalogue No. 87972, manufactured by Fluka). When a mixed medium (DF medium) consisting of a DMEM medium and a Ham's F-12 medium, to which soybean peptone was added, is used, the mixing weight ratio of the two mediums is preferably from 3:1 to 1:3, more preferably 1:1. The final concentration of soybean peptone in the mixed medium is preferably 250 μg/ml to 3,000 μg/ml, more preferably about 750 μg/ml.

Then, the cells are adapted to a medium (DFSP medium) prepared by adding plural kinds of soybean-derived peptones to a mixture of a Dulbecco's modified Eagle medium (DMEM medium) and Nutrient Mixture (Ham's F-12), both of which are serum-free media. The mixing weight ratio of DMEM medium and Ham's F-12 is preferably from 3:1 to 1:3. Plural kinds of soybean-derived peptones are used. Examples of the soybean-derived peptones include, but are not limited to, soybean peptone (Peptone from soybean, enzymatic digest, Catalogue No. 87972, manufactured by Fluka), Polypeptone S (POLYPEPTON-S, Catalogue No. 391-00125, manufactured by Nihon Pharmaceutical Co., Ltd.), Peptone Hy-Soy (trade name, Product No. P6463-250G, manufactured by Sigma), Phytone (manufactured by BBL) and Soytone (manufactured by Difco) Among those mentioned above, a combination of Peptone from soybean and Polypeptone S is preferable. The total amount of soybean peptones added is preferably 250 μg/ml to 3,000 μg/ml, more preferably about 1,500 μg/ml, based on the medium.

The medium may contain additives such as antibiotics as long as it does not contain animal-derived proteins.

The composition of the DFSP medium includes, but is not limited to, the following:

(One Example of Preparation of the DFSP Medium)

1) A Dulbecco's modified Eagle medium (DMEM, Catalogue No. 11885, manufactured by Invitrogen) is prepared.

2) F-12 Nutrient Mixture (Ham's F-12, Catalogue No. 11765, manufactured by Invitrogen) is prepared.

3) A mixture of equal amounts of DMEM and Ham's F-12 is prepared.

4) 15 g of soybean peptone (Peptone from soybean, enzymatic digest, Catalogue No. 87972, manufactured by Fluka) is dissolved in 1,000 ml sterilized distilled water and filtered through a 220-nm filter, and the resulting filtrate is added to the medium in 3) above, in an amount of 5 ml per 100 ml of the medium (final concentration: 750 μg/ml).

5) 15 g of soybean peptone Polypeptone S (POLYPEPTON-S, Catalogue No. 391-00125, manufactured by Nihon Pharmaceutical Co., Ltd. and sold by Wako Pure Chemical Industries, Ltd.) is dissolved in 1,000 ml sterilized distilled water and filtered through a 220-nm filter, and the resulting filtrate is added to the medium in 3) above, in an amount of 5 ml per 100 ml of the medium (final concentration: 750 μg/ml).

6) When L-glutamine is not contained in DMEM and Ham's F-12 medium, L-glutamine is added at a concentration of 300 mg/L (final concentration: 300 µg/ml).

7) As antibiotics, potassium penicillin G, streptomycin sulfate, and amphotericin B are added to the medium to concentrations of 100 U/ml, 100 µg/ml and 2.5 µg/ml, respectively (all these concentrations are the final concentration).

The feline cells capable of culture without animal-derived proteins can be obtained in the following manner. First, fcwf-4 cells are subcultured in a VP-SFM medium containing fetal bovine serum at a concentration of 0.25% until the passage number reaches 5, then the cells are further subcultured in a VP-SFM medium containing fetal bovine serum at a concentration of 0.1% until the passage number reaches 5, and then the cells are subcultured in a VP-SFM medium containing fetal bovine serum at a concentration of 0.05% until the passage number reaches 9. Then, the cells are subcultured in a DF medium containing 750 µg/ml soybean peptone and a mixture of DMEM medium and Ham's F-12 medium in the ratio of 1:1, until the passage number reaches 21. Then, the cells are subcultured in a DFSP medium containing 750 µg/ml soybean peptone (Peptone from soybean) and 750 µg/ml Polypeptone S and a mixture of DMEM medium and Ham's F-12 medium in the ratio of 1:1, whereby a newly induced cell strain that has been adapted to the DFSP medium can be obtained. These cells are further subcultured until the passage number reaches 25. The applicant has internationally deposited the resulting cell, designated fcwf-SF strain, under Accession No. FERM ABP-10594 since Mar. 31, 2006, with International Patent Organism Depositary (IPOD), National Institute of Advanced Industrial Science and Technology (AIST), Higashi 1-1-1, Tsukuba City, Ibaraki Pref., Japan.

The fcwf-SF cell strain is infected with a virus that is sensitive to fcwf-4 cell strain, and the thus infected cell strain can be cultured and multiplied to produce the virus. The medium used in culturing the virus is preferably a medium that does not contain animal-derived proteins, more preferably the aforementioned DFSP medium.

The culture vessel used for cell culture may be either a plastic vessel or a glass vessel. Examples of the culture vessel include a non-glass vessel, for example, a plastic vessel such as a 25-cm$^2$ T flask or a plastic Petri dish with a diameter of 6 cm and the corresponding regenerable vessel made of glass. Particularly, a disposable plastic culture vessel in which uniform culture conditions can be easily obtained is preferable.

Known methods can be used in the culture of the infected cell strain. Examples of such known methods include a monolayer culture method and a suspension culture method.

For example, the monolayer culture method comprises infecting cells that have been monolayer-cultured in the inner surface of a vessel with a virus of interest and then subjecting the infected cells to stationary culture or rotation culture, so as to prepare the virus in the culture supernatant. As a vessel, a plate culture vessel or a roller culture flask for example can be used. Specific examples of such a vessel include a Petri dish and a T flask. The material of such a vessel is preferably a non-glass material, more preferably a plastic.

An example of the suspension culture method is a microcarrier method using micro carrier beads. The microcarrier method involves, for example, allowing cells to proliferate in the form of a monolayer on the surfaces of microcarrier beads in a bioreactor (culture tank), and then infecting the cells proliferated on the microcarrier beads with viruses, followed by culturing the cells under stirring, thereby preparing viruses of interest in the culture solution. Examples of materials of such microcarrier beads include ceramic, dextran, glass, silicon, plastic, and polyacrylamide. Examples of commercially available beads can include Cytodex (trade name) 1 manufactured by Amersham Bioscience.

The virus that is sensitive to fcwf-4 cells include, but are not limited to, viruses which infect many cats (*Felis catus*) and animals of the cat family, including not only feline panleukopenia virus that is a virus of Parvoviridae, feline herpesvirus-1 (also called feline viral rhinotracheitis virus) that is a virus of Herpesviridae, and feline calicivirus that is a virus of Caliciviridae, but also a wide variety of viruses of Coronaviridae. The fcwf-4 cells are also sensitive to particularly coronaviruses belonging to group 1 coronaviruses such as feline enteric coronavirus, feline infectious peritonitis virus, canine coronavirus, transmissible gastroenteritis virus of swine, porcine epidemic diarrhea virus, and group 2 coronaviruses such as bovine coronavirus.

A virus produced by the method of the present invention can be recovered and purified for use as a vaccine or a diagnostic antigen substance. For recovery and purification of the virus, known methods can be used. For example, cells are disrupted by freezing and thawing, and the resulting thawed solution is then centrifuged to eliminate cells or disrupted cell debris, and the supernatant may be recovered as a virus stock.

When a vaccine is produced from the above virus, the produced vaccine may be either an inactivated vaccine or a live vaccine. When an inactivated vaccine is produced, the recovered and purified virus may be inactivated with formalin or the like, and an adjuvant may be added to the inactivated virus. On the other hand, when a live vaccine is produced, an attenuated virus may be produced, and it may be then recovered and purified. Thereafter, an adjuvant may be added to the resultant virus, if necessary. The viral content in a vaccine should be a level sufficient for endowing a cat to which the vaccine is to be administered, with immunity that is necessary for inhibiting infection with the virus as a target. In general, such a viral level is between $1 \times 10^{3.5}$ TCID$_{50}$/ml and $1 \times 10^{5.0}$ TCID$_{50}$/ml, or more. An example of the adjuvant used herein is an adjuvant that is able to induce systemic protective immunity or local protective immunity to a cat to which the vaccine is to be administered.

For production of a diagnostic reagent for infections or for a diagnostic examination method using the same, the inactivated virus as stated above is used as an antigen, or an antigen isolated from the virus is fixed on a support such as an ELISA plate or a nitrocellulose membrane, thereby preparing the diagnostic reagent. The diagnostic reagent is bound to an antibody existing in the serum of a cat, following reacting with a secondary antibody having horseradish peroxidase or alkaline phosphatase bound thereto, and then subjected to a known reaction such as a color reaction to enable visualization thereof. Thus, the presence or absence of an antibody in a cat infected with various types of viruses, namely, the presence or absence of infection, can be detected and confirmed.

When the cells are to be cryopreserved, a medium prepared by adding dimethyl sulfoxide (DMSO) to the DFSP medium in the present invention can be used. DMSO is available from Wako Pure Chemical Industries, Ltd. (Catalogue No. 043-07216). The concentration of DMSO is preferably 7.5% to 20%, more preferably about 10%, in the DFSP medium.

Hereinafter, the present invention will be described in more detail by reference to the Examples. However, these examples are not intended to limit the scope of the present invention.

The term "%" used in the present specification means "% by weight" unless otherwise specified.

Example 1

Creation of fcwf-SF Strain by Using a DFSP Medium

In a first step of adaptation, fcwf-4 cells were subcultured in a commercial medium containing fetal bovine serum while the concentration of fetal bovine serum was gradually decreased. That is, the cells were subcultured in a medium prepared by adding 0.25% fetal bovine serum to a commercial medium "VP-SFM" (Catalogue No. 11681-020, manufactured by Invitrogen) containing 10 ng/ml recombinant epidermal growth factor for 5 generations, then the cells were subcultured in a VP-SFM medium containing fetal bovine serum at a concentration of 0.25% for 5 generations, and at a concentration of 0.05% for 9 generations. When the VP-SFM medium was made completely free of serum, the cells could not be subcultured in the medium.

The fcwf-4 cells used in this example were those used in the 1990s by the present inventor in the Lab. of Veterinary Microbiology, Department of Veterinary Medicine, Faculty of Agricultural, Kagoshima University, and the present inventor obtained the fcwf-4 cells from Professor Hiroyuki Koyama, the Lab. of Veterinary Infectious Diseases, Kitasato University, who had acquired the cells with the permission of Professor Niels C. Pedersen, the Lab. of Internal Medicine, Department of Veterinary Medicine, University of California, USA. Thereafter, the fcwf-4 cells were transferred to the Lab. of Clinical Microbiology, Kyoritsu Seiyaku Corp. In the Lab. of Clinical Microbiology as the final holder, from April 1995, the cells have been subcultured in a medium (7.5% MEM) produced by adding 7.5% fetal bovine serum, 10% tryptose phosphate broth, and L-glutamine (0.292 g/L), and for the purpose of prevention of bacteria's contamination, also adding penicillin (100 U/ml), streptomycin (100 µg/ml), and amphotericin B (0.25 to 0.5 µg/ml), to an Eagle's MEM basal medium (Eagle MEM medium "Nissui" (1), manufactured by Nissui Pharmaceutical Co., Ltd.).

When the parent cells (fcwf-4 cells), and fcwf-SF cells derived therefrom and adapted to a serum-free medium, were subcultured in this example, the cell surfaces were washed twice with a 0.25% trypsin+0.02% EDTA (ethylenediaminetetraacetic acid) solution, and the cells were then left in an incubator at 37° C., so that the cells were dispersed. The used trypsin was swine pancreas-derived DIFCO TRYPSIN 250 (Difco Co., Ltd.). The above trypsin was dissolved in sterilized PBS and was then filtrated through a 220-nm filter for sterilization.

Then, the fcwf-4 cells that had been adapted to the VP-SFM medium containing 0.05% fetal bovine serum were used in adaptation to a commercial medium. That is, the fcwf-4 cells were subcultured until the passage number reached 21 in a medium prepared by adding soybean peptone (Peptone from soybean, enzymatic digest, Catalogue No. 87972, manufactured by Fluka) to a mixture of DMEM Medium (Catalogue No. 11885-084, manufactured by Invitrogen) and Nutrient Mixture (Ham's F-12, Catalogue No. 11765-054, manufactured by invitrogen) (DF medium) The weight ratio of DMEM Medium and Ham's F-12 was 1:1. The final concentration of soybean peptone in the medium was 750 µg/ml.

While the cells were subcultured until the passage number reached 21, the cells were treated under basically the same subculture conditions as those for the parent cells. That is to say, the original cells were subcultured to quantities that were 3 to 4 times the initial quantities at the intervals of approximately 4 to 5 days. As often observed in the process of cell adaptation, cell growth was delayed at times. Thus, during such delay, the medium was exchanged with a fresh medium once or twice, or the expanding factor was reduced to 2 or 3 times, so as not to interrupt the cell growth.

The growth of fcwf-4 cells could not be sufficiently promoted where commercially available Eagle's MEM, RPMI 1640 Medium, McCoy's 5A Medium, Leiovitz's L-15 Medium, Dulbecco's modified Eagle medium (DMEM) or Nutrient Mixture (Ham's F-12) was used alone, and thus the growth of the cells was terminated within the passage number reached 2 or 3.

When the weight ratio of DMEM Medium and Ham's F-12 was changed even in the range of 1:3 to 3:1, the fcwf-4 cells grew in a similar manner.

Then, the fcwf-4 cells that had been adapted to the DF medium were subcultured until the passage number reached 9 in a medium (DFSP medium) prepared by adding Polypeptone S (POLYPEPTON-S, Catalogue No. 391-00125, manufactured by Nihon Pharmaceutical Co., Ltd.) to the DF medium. Polypeptone S is powder produced by enzymatically degrading defatted soybeans, then purifying the product and drying it. Polypeptone S was added at a final concentration of 750 µg/ml to the medium. The composition of the DFSP medium used herein is shown in Table 1.

TABLE 1

One Example of Composition of the DFSP Medium

1) A Dulbecco's modified Eagle medium (DMEM, Catalogue No. 11885, manufactured by Invitrogen).
2) F-12 Nutrient Mixture (Ham's F-12, Catalogue No. 11765, manufactured by Invitrogen).
3) A mixture of equal amounts of DMEM and Ham's F-12 is prepared.
4) 15 g of soybean peptone (Peptone from soybean, enzymatic digest, Catalogue No. 87972, manufactured by Fluka) is dissolved in 1,000 ml sterilized distilled water and filtered through a 220-nm filter, and the resulting filtrate is added to the medium in 3) above, in an amount of 5 ml per 100 ml of the medium (final concentration: 750 µg/ml).
5) 15 g of soybean peptone Polypeptone S (POLYPEPTON-S, Catalogue No. 391-00125, manufactured by Nihon Pharmaceutical Co., Ltd.) is dissolved in 1,000 ml sterilized distilled water and filtered through a 220-nm filter, and the resulting filtrate is added to the medium in 3) above, in an amount of 5 ml per 100 ml of the medium (final concentration: 750 µg/ml).
6) When L-glutamine is not contained in DMEM and Ham's F-12 medium, L-glutamine is added at a concentration of 300 mg/L (final concentration: 300 µg/ml).
7) As antibiotics, potassium penicillin G, streptomycin sulfate, and amphotericin B are added to the medium to concentrations of 100 U/ml, 100 µg/ml and 2.5 µg/ml, respectively (all these concentrations are the final concentration).

When the above cells were subcultured in the DFSP medium until the passage number reached 9 (or in a serum-free state, the passage number reached 30 in total), it was confirmed that the cells were clearly adapted to the above medium, and that the cell growth could be stabilized. That is to say, the time required for formation of cell sheets and the passage intervals became constant over the past several passages, and the cells were subcultured to quantities that were 3 to 4 times the initial quantities at the intervals of 5 to 7 days. Two or three days after culturing, the medium was exchanged once with a fresh one, and when the cells were cultured therein for 2 to 3 days, the cells could thereafter be subcultured. At this time point, the cells had been adapted to the DFSP medium (i.e. a serum-free medium), and the thus newly induced cell strain was designated "fcwf-SF strain".

Figure 1:
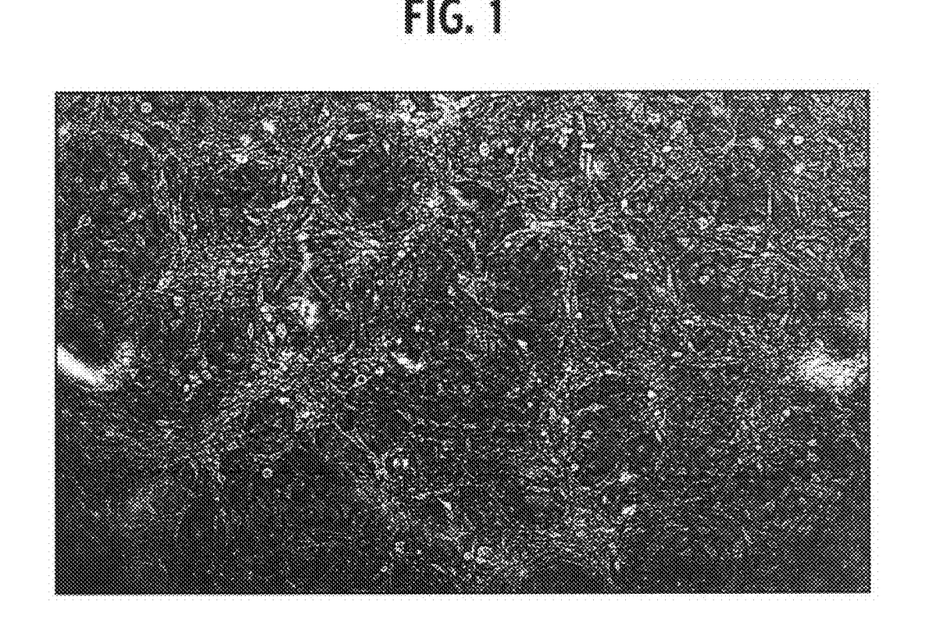
FIG. 1 is a photograph of the 30th-generation fcwf-SF cells taken on the 4th day of culture (day after medium replacement 3 days after culture was initiated).

The cells from the 31st-generation were used to examine their characteristics. FIG. 1 shows a photograph of a cell sheet taken on the 4th day of culture of the 30th-generation fcwf-SF cells (day after medium replacement 3 days after culturing). The photograph was taken under an inverted microscope, while the cells were neither fixed nor stained. As compared with the parent cells cultured in 7.5% MEM medium to which fetal bovine serum had been added, the fcwf-SF cells, as registered with ATCC, had a characteristic closer to a morphological characteristic ("spindle- to star-shaped") of the original cells.

Figure 2:
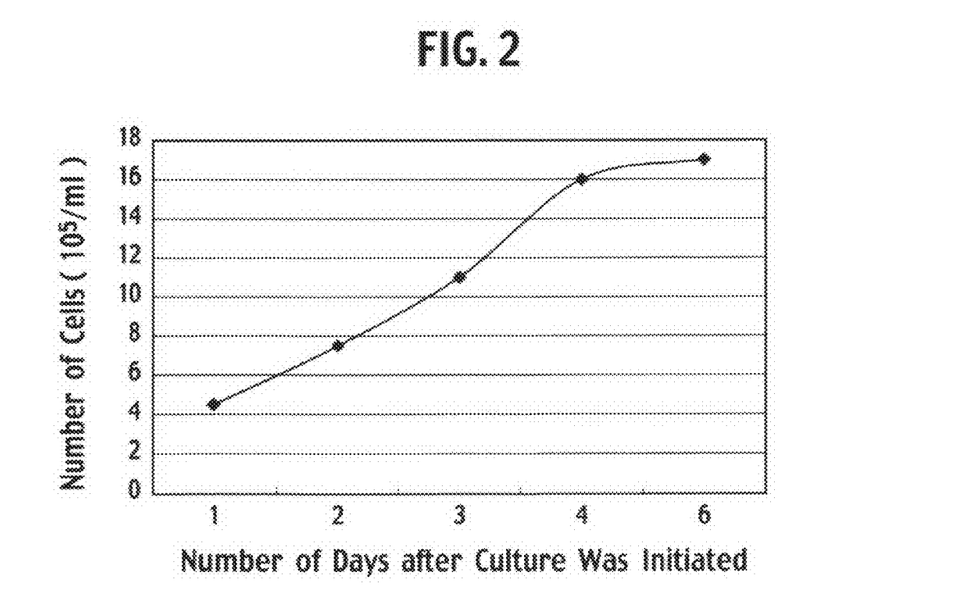
FIG. 2 shows a growth curve of the 34th-generation fcwf-SF cells subcultured in a DFSP medium.

FIG. 2 shows a growth curve of the 34th-generation fcwf-SF cells. A cell suspension at a density of $4.5 \times 10^5$ cells/ml was subjected to stationary culture in a 25-cm$^2$ T flask in an open system, and the number of cells was measured every 24 hours. As shown in FIG. 2, the number of fcwf-SF cells was increased about 4-fold after 6 days.

Other characters of fcwf-SF cells and culture system are shown below.

A disposable plastic culture vessel in which uniform culture conditions can be easily obtained was used in this example.

Although culture can be conducted both in a closed system or in an open system (in a 5% $CO_2$ incubator), culture in the DF medium was conducted in a closed system while culture, while in the DFSP medium was conducted in an open system where the pH of the medium can be easily controlled in order to collect data.

The cells did not grow in the DFSP medium from which soybean peptone had been removed.

Even when the amounts of the 2 types of soybean-derived peptones in the DFSP medium were made twice (1.5 mg/ml) respectively, cell-proliferating potency was not changed.

The cells did not grow sufficiently when the RPMI 1640 medium to which the 2 types of soybean-derived peptones had been added was used in place of the mixed medium of DMEM and Ham's F-12.

Changes were not observed particularly even when soybean hydrolysates (P6463 Peptone Hy-Soy T, Sigma-Aldrich) or a malt extract (Bacto (trade name) Malt Extract, Catalogue No. 218630, Becton, Dickinson and Company) was further added to the DFSP medium.

There was no good effect on the growth or form of the cells, even when a yeast extract (Bacto (trade name) Yeast Extract, Catalogue No. 212750, Becton, Dickinson and Company) and a wheat extract (HyPep 4601 (trade name) Protein Hydrolysate from heat gluten, Sigma-Aldrich) were further added to the DFSP medium. Such addition appeared to rather adversely affect the growth speed and morphology of the cells.

The applicant has internationally deposited the fcwf-SF strain cells (those cells that were obtained by continuous culture until the passage number reached 46 (that is, the passage numbers in the DF medium and DFSP medium were 21 and 25, respectively)) under Accession No. FERM ABP-10594 since Mar. 31, 2006, with International Patent Organism Depositary (IPOD), National Institute of Advanced Industrial Science and Technology (AIST), Higashi 1-1-1, Tsukuba City, Ibaraki Pref., Japan.

Example 2

Cryopreservation of the fcwf-SF Cells

A medium used in cell freezing was prepared by adding 10% DMSO (Catalogue No. 043-07216, manufactured by wako Pure Chemical Industries, Ltd.) to a DFSP medium. The fcwf-SF cells were suspended at a density of more than $10^6$ cells/ml in the prepared medium. Then, the resulting suspension was dispensed in cryopreserving vials in a volume of 1.8 ml per vial. Each vial was placed in a simple cell freezer "BICELL (trade mark)" (Nihon Freezer Co., Ltd.) that had been chilled in a refrigerator, and the vial was then frozen with a freezer of $-80°$ C. overnight. Thereafter, the frozen cells were transferred to liquid nitrogen (liquid phase) in which the cells could be cryopreserved.

48 hours later, in order to confirm a state of cryopreservation, the frozen cells were removed from the liquid nitrogen according to routine methods, and the cells were then immediately thawed in warm water at approximately 40° C. Thereafter, the thawed cells were diluted and suspended in 10 ml of DFSP medium, and the cells were then recovered by low-speed centrifugation. A cell pellet was resuspended in 7.5 ml of DFSP medium, and the suspension was then placed in a 25-cm$^2$ T flask. The flask was cultured at 37° C.

On day 3 of culturing, a cell sheet was formed. On day 5, the cells were subcultured in a new medium having a volume 4 times the volume of the previous medium. Three days after the subculture, the thus subcultured cells also formed a cell sheet. No adverse effects of this freezing method were found as far as the cells were observed at least under a microscope. Then, subculturing could be carried out as in the case of non-frozen cells. From such results, it was confirmed that a 10% DMSO-added DFSP medium could be effectively used in freezing the fcwf-SP cells of the present invention.

Example 3

Production of Serum-Free Seed Virus Stock

Viruses which currently constitute core vaccines used for pet cats widely all over the world are 3 types of viruses, that is, feline herpesvirus-1, feline calicivirus, and feline panleukopenia virus. There is also a vaccine against feline infectious peritonitis virus that is a feline coronavirus infecting a cat to cause fatal feline infectious peritonitis. To date, such virus stocks have been multiplied in a cell culture system such as Eagle's MEM to which fetal bovine serum or tryptose phosphate broth had been added. Thus, in order to cultivate viruses in a serum-free medium as a cell culture system, animal proteins such as a bovine serum ingredient should be eliminated. Hence, a serum-free seed virus stock was produced in the following manner. Table 2 shows the actually used virus strain names, among the aforementioned virus species, and the virus titers of seed virus stocks produced using such virus strains.

TABLE 2

Viruses and Infectivity Titers of Seed Virus Stocks

| | | Infectivity titer (TCID$_{50}$/0.1 ml) | |
|---|---|---|---|
| Virus | Strain name | 7.5% MEM medium | DFSP medium |
| Feline herpesvirus-1 | C7301 | $10^{5.0}$ | $10^{7.5}$ |
| Feline calicivirus | F9 | $10^{6.0}$ | $10^{8.7}$ |
| Feline panleukopenia virus | TU-1 | $10^{5.7}(256)$* | $10^{4.5}(32)$* |
| Feline infectious peritonitis virus (type 2) | M91-267 | $10^{7.5}$ | $10^{4.5}$ |

*Hemagglutination titer is shown in parentheses.

With regard to the initial virus stocks of feline herpesvirus-1, feline calicivirus and feline infectious peritonitis virus, fcwf-4 cells as parent cells after inoculation with the viruses were cultured in a medium to which 2% fetal bovine serum and 10% tryptose phosphate broth had been added, so as to promote multiplication of the viruses. Thus, since 2% bovine serum and 10% tryptose phosphate broth are contained in the culture supernatant, the following attempt was made to eliminate the influence of such ingredients. A virus stock was inoculated into fcwf-SF cells which had been cultured in a closed system flask and had formed a cell sheet, and viruses were then adsorbed thereon for 1 hour. Thereafter, the virus unadsorbed was eliminated by aspiration, and the cell surfaces were then washed twice with a DFSP medium. Thereafter, a DFSP medium was added thereto, and then subjected to stationary culture in an incubator at 37° C., so as to promote multiplication of viruses. With regard to feline panleukopenia virus, the virus was inoculated into the cells when the cells were suspended in the medium. The initial virus stock contained 7.5% fetal bovine serum, and thus the influence of the bovine serum in the initial virus stock was greater than that in other virus stocks. Hence, when the fcwf-SF cells were suspended in the DFSP medium, a virus stock in an amount of approximately 5% of the culture solution was added to the suspension, and the mixed solution was then subjected to stationary culture in an incubator at 37° C. Twenty-four hours after adhesion of the cells to the wall, the culture solution was eliminated by aspiration, and the cell surfaces were washed once with a DFSP medium. Thereafter, a new DFSP medium was added to the incubator to promote multiplication of the virus. Several to seven days later, the culture in a flask was once frozen and thawed. The thawed solution was subjected to low-speed centrifugation to eliminate cells and cell debris. The supernatant was defined as a 2nd-generation virus stock. This operation was repeated two times in total, and the obtained 3rd-generation culture supernatant was defined as a serum-free virus stock, and it was poured in a freezer at −80° C. and was preserved.

For comparison, virus stocks were prepared and stored in the same manner as above except that an MEM medium containing 7.5% fetal bovine serum was used in place of the DFSP medium, and fcwf-4 cells were used in place of the fcwf-SF cells.

The virus titers obtained for each virus are shown in Table 2. With respect to the infectivity titers of virus species produced in the fcwf-SF cells cultured in the DFSP medium, the infectivity titers of feline panleukopenia virus and feline infectious peritonitis virus were also high similar to those of the viruses replicated in fcwf-4 cells as parent cells, and particularly the virus stocks of feline herpesvirus-1 and feline calicivirus produced in the fcwf-SF cells possessed infectivity titers that were 300 to 5,000 times higher than those of the viruses in the parental fcwf-4 cells.

Example 4

Feline Herpesvirus-1

1) The fcwf-4 cells used as parent cells in a 7.5% MEM medium (Comparative Example) and the fcwf-SF cells in a DFSP medium (Example) were cultured respectively in a 25-cm$^2$ T flask in a 5% $CO_2$ incubator. Five days after initiation of the culture, a sheet was formed. At that time, the number of cells was counted.

2) A feline herpesvirus-1 C7301 strain, from the virus stocks as shown in Table 2, was diluted and then inoculated into the two above types of cells such that the two types of cells could have the same m.o.i. (multiplicity of infection; the ratio of the number of infective viral particles and a known number of cultured cells), which was 0.01.

3) After the viruses had been adsorbed at 37° C. for 1 hour, unadsorbed viruses were eliminated by aspiration. Thereafter, 7.5% MEM or a DFSP medium was added to the flask, followed by stationary culture.

4) Subsequently, after inoculation at the intervals of 24 hours, the culture contained in the flask was cryopreserved in a freezer at −80° C. on the 1st, 2nd, 3rd, 4th, and 6th days.

5) Before the measurement of virus infectivity titers, the frozen flask was thawed at room temperature, and a supernatant obtained by eliminating cell components by centrifugation at 2,500 rpm for 10 minutes was then used in the measurement of an infectivity titer.

6) Such an infectivity titer was measured by a micro-titration method using a 96-well microplate. That is to say, the virus stock obtained in 5) above was diluted 10 times with 7.5% MEM medium by serial dilution, and 100 μl of each dilution was added to 4 wells. Thereafter, 100 μl of a cell suspension was further added to every well, and the obtained mixture was lightly blended, followed by stationary culture in a 5% $CO_2$ incubator at 37° C.

7) As such a cell suspension, the fcwf-4 cells were suspended at a density of 1×10$^5$ cells/ml in 7.5% MEM medium.

8) Seven days after virus inoculation, the end point of an infectivity titer was calculated based on the presence or absence of cytopathic effect (CPE) caused by the virus.

Figure 3:
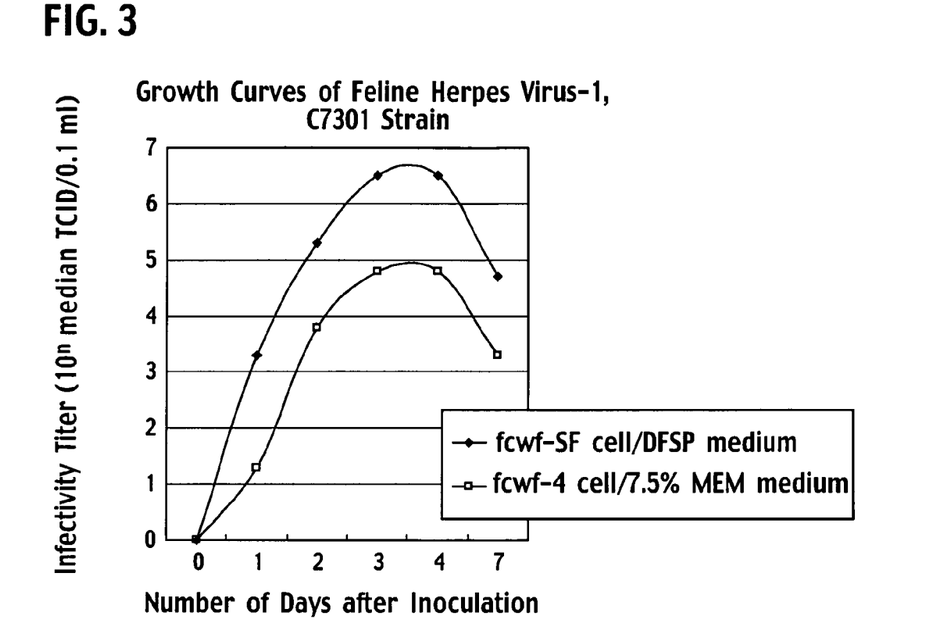
FIG. 3 shows growth curves of feline herpes virus-1, C7301 strain, in parent cells (i.e. fcwf-4 cells) cultured in 7.5% MEM (Eagle's MEM medium supplemented with 7.5% fetal bovine serum) and in fcwf-SF cells cultured in a DFSP medium.

FIG. 3 shows growth curves of the feline herpesvirus-1 C7301 strains in the fcwf-4 cells as parent cells cultured in 7.5% MEM and in the fcwf-SF cells cultured in the medium of the present invention that contained no proteins derived from animals. From the day after virus inoculation, production of the virus was initiated in both the parent fcwf-4 cells and the fcwf-SF cells, and thereafter, the number of the viruses increased. At all time points, the fcwf-SF cells exhibited virus infectivity titers that were 25 to 100 times higher than those of the fcwf-4 cells.

Example 5

Feline Calicivirus

The infectivity titer was examined in the same manner as in Example 4 except that:

1) the virus strain used was a feline calicivirus F9 strain.

Figure 4:
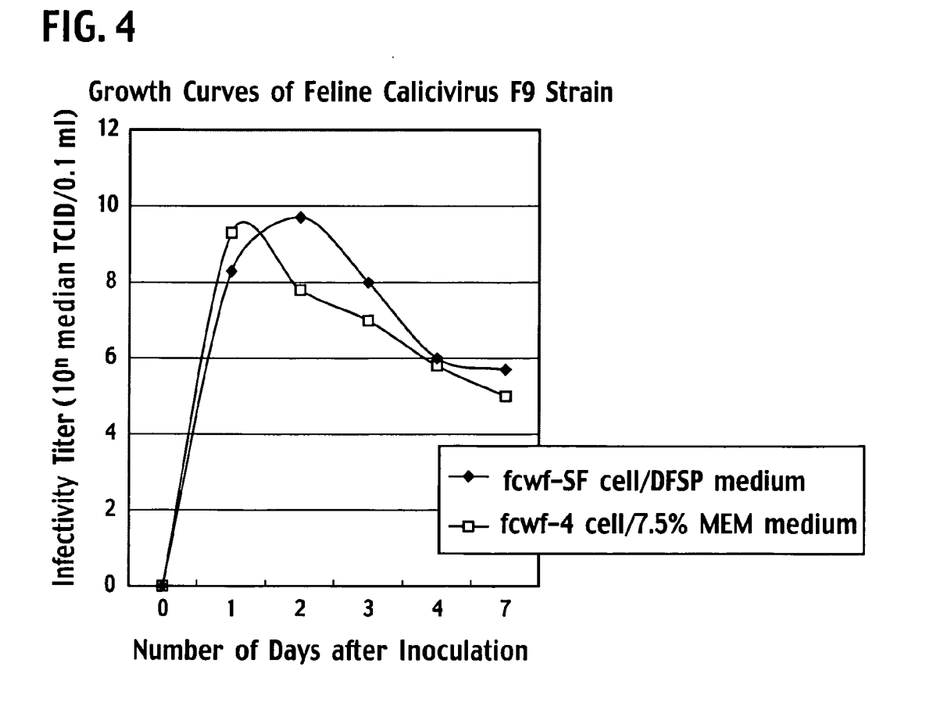
FIG. 4 shows growth curves of feline calicivirus F9 strain in parent cells (i.e. fcwf-4 cells) cultured in 7.5% MEM and in fcwf-SF cells cultured in a DFSP medium.

The results are shown in FIG. 4. In both the cultured cells, the virus was multiplied in almost the same manner, to show an excellent infectivity titer similar to that in the previous viral culture method using bovine serum. Specifically, the time required for reaching the peak of virus multiplication was 1 day later in fcwf-SF cells, but the viral titer was slightly ($10^{0.4}$) higher.

Example 6

Feline Infectious Peritonitis Virus

The same method as in Example 4 was applied herein with the following two exceptions:

1) the virus strain used in preparing a viral growth curve was a feline infectious peritonitis virus M91-267 strain that is type 2 feline coronavirus;

2) immediately after viral inoculation, the cells underwent a cytopathic effect to detach from a wall of the flask, and thus the culture contained in a flask was cryopreserved in a freezer at −80° C. on the 1st, 2nd, 3rd and 4th days after the inoculation, and 3) feline infectious peritonitis virus Yayoi strain, that is, type 1 feline coronavirus was also used in examination of the virus sensitivity of fcwf-SF cells.

Figure 5:
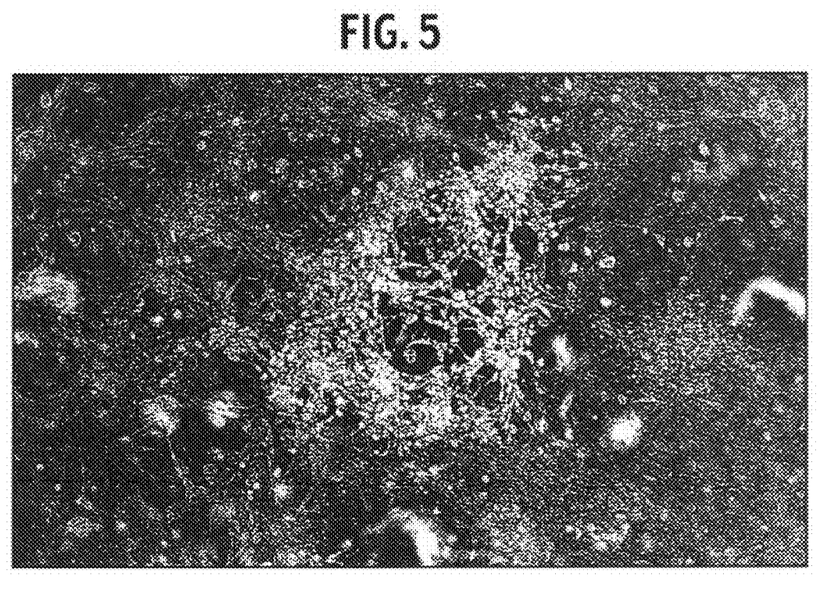
FIG. 5 is a photograph showing CPE exhibited accompanying the growth of feline infectious peritonitis virus Yayoi strain (type 1 feline coronavirus) in fcwf-SF cells.
Figure 6:
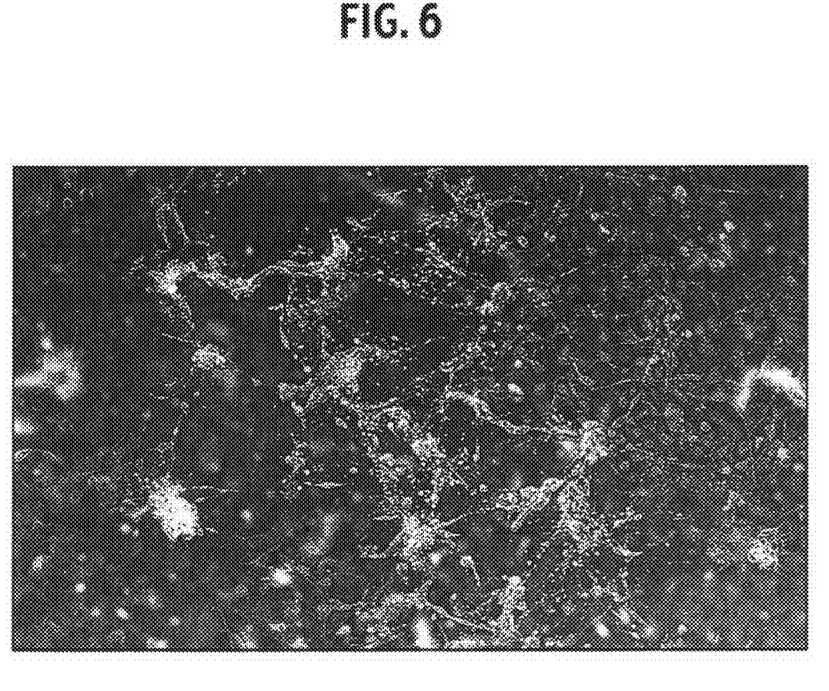
FIG. 6 is a photograph showing CPE exhibited accompanying the growth of feline infectious peritonitis virus M91-267 strain (type 2 feline coronavirus) in fcwf-SF cells. This CPE is cytolytic CPE similar to that of type 1 feline coronavirus, and formation of multinuclear giant cells was not significant.

FIG. 5 shows CPE exhibited accompanying the growth of feline infectious peritonitis virus Yayoi strain (that is, type 1 feline coronavirus) in fcwf-SF cells, and FIG. 6 shows CPE exhibited accompanying the growth of feline infectious peritonitis virus M91-267 strain (that is, type 2 feline coronavirus) in fcwf-SF cells.

Type 1 feline coronavirus is characterized by being difficult to grow in cell culture, but the Yayoi strain was multiplied to exhibit CPE in the fcwf-SF cells cultured in a DFSP medium, as shown in the FIG. 5. Although the degree of multiplication was not numerically expressed, the degree was almost the same as that in the fcwf-4 cells as parent cells.

Figure 7:
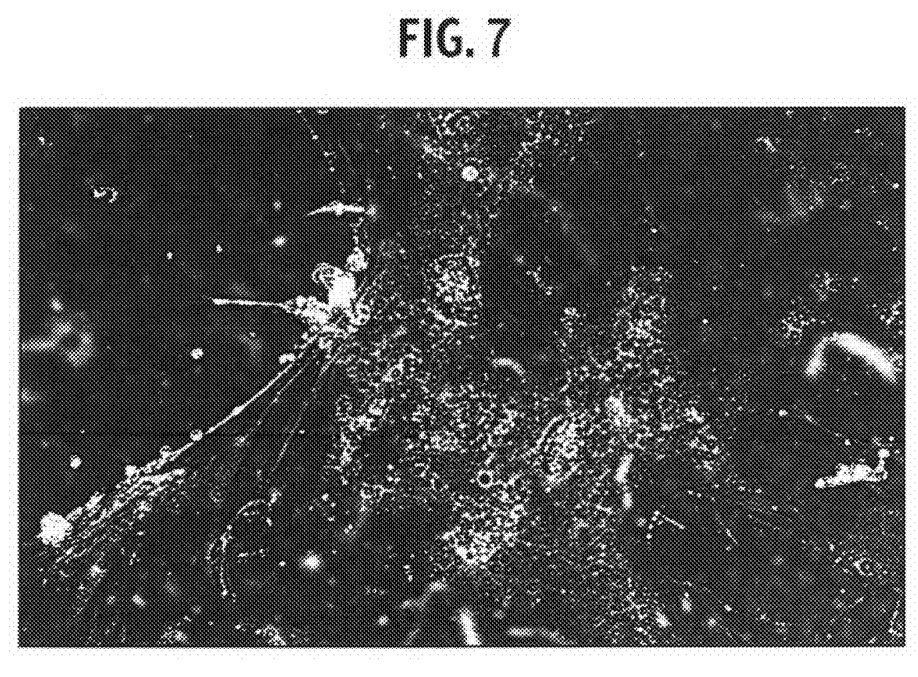
FIG. 7 is a photograph showing CPE exhibited accompanying the growth of feline infectious peritonitis virus M91-267 strain (type 2 feline coronavirus) in fcwf-4 cells. This CPE is characterized by formation of multinuclear giant cells.

On the other hand, it is well-known that the proliferating potency of type 2 feline coronavirus is generally good in fcwf-4 cells as well, and as shown in FIG. 6, this virus grew with CPE even in fcwf-SF cells as well. However, CPE in fcwf-4 cell culture is characterized by formation of multinuclear giant cells (FIG. 7), while CPE in fcwf-SF cell culture is cytolytic CPE similar to that of type 1 feline coronavirus, and formation of multinucleate giant cells was not obvious.

Figure 8:
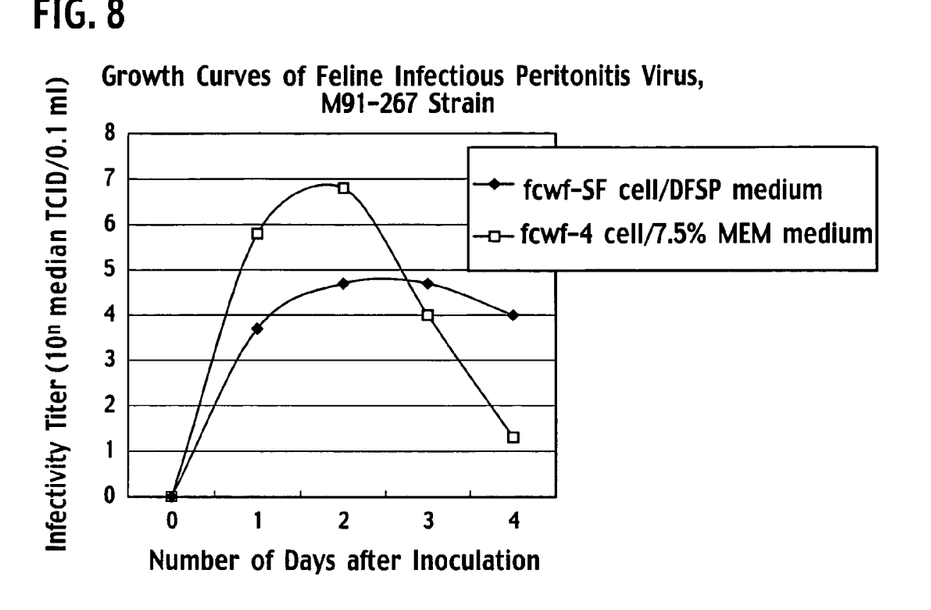
FIG. 8 shows growth curves of feline infectious peritonitis virus M91-267 strain in parent cells (i.e. fcwf-4 cells) cultured in 7.5% MEM and in fcwf-SF cells cultured in a DFSP medium.

FIG. 8 shows growth curves of feline infectious peritonitis virus M91-267 strain (type 2 feline coronavirus) in the parent cells (i.e. fcwf-4 cells) and in the newly invented fcwf-SF cells cultured in the animal-derived protein-free DFSP medium in the invention. In both the cases, the virus titer reached a peak two days after inoculation, and then decreased. In fcwf-SF cell culture, sufficient viral multiplication was exhibited.

Example 7

Feline Panleukopenia Virus

The same method as in Example 4 was applied herein with the following four exceptions:

1. The used virus strain was a feline panleukopenia virus TU-1 strain;

2. When the cells were suspended in a medium, viral inoculation was conducted before stationary culture was initiated;

3. Thereafter, the cells were subjected to stationary culture in an incubator at 37° C., and 24 hours culture after adhesion of the cells to the wall, the culture solution was eliminated by aspiration, and the cell surfaces were washed once with a new medium, and a new medium was added again to the cells to reduce the influence of the remaining virus, the time point of which was regarded day 0; and 4. An infectivity titer was determined by the micro-titration method according to the presence of a hemagglutinin generated in a supernatant contained in each well. That is, 50 μl of the supernatant was collected from each well, and it was then transferred to a microplate that had been separately prepared for hemagglutination reaction. Thereafter, an equal amount of phosphate buffered saline (PBS), pH 6.8 and an equal amount of rhesus blood cell suspension were added to every well. The rhesus blood cell suspension was prepared by suspending 0.75% blood erythrocytes in the same type of PBS. The obtained mixture was fully stirred, and it was then left at 4° C., and the infectivity titer was calculated based on the presence or absence of hemagglutination.

Figure 9:
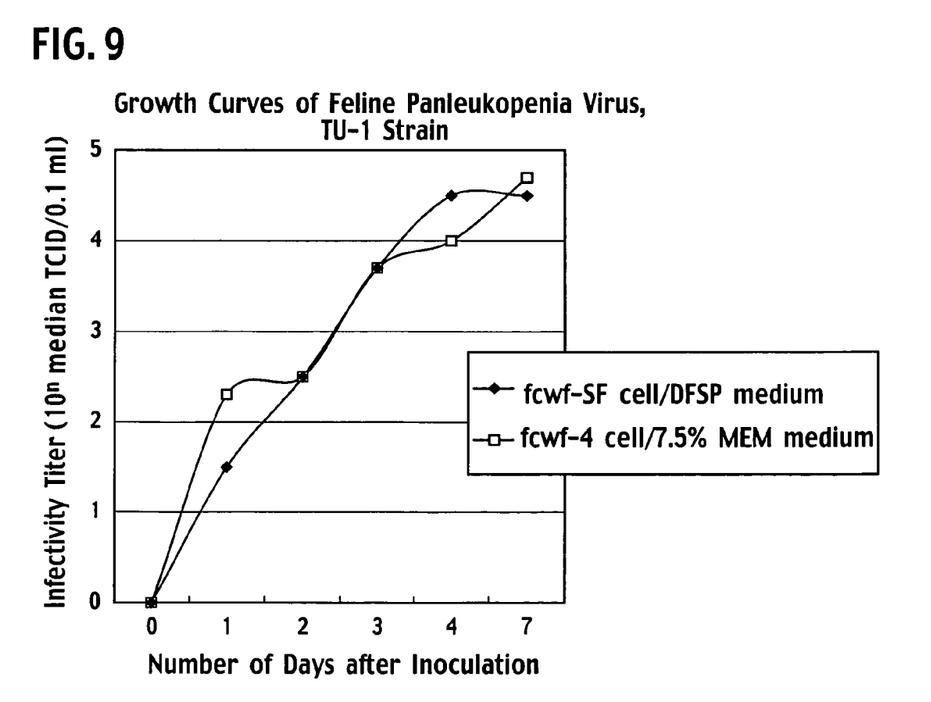
FIG. 9 shows growth curves of feline panleukopenia virus TU-1 strain in parent cells (i.e. fcwf-4 cells) cultured in 7.5% MEM and in fcwf-SF cells cultured in a DFSP medium.

The results are shown in FIG. 9. An excellent growth phase was shown similarly by the feline panleukopenia virus TU-1 strain not only in the parent cells (i.e. fcwf-4 cells) but also in fcwf-SF cells cultured in the animal-derived protein-free DFSP medium.

INDUSTRIAL APPLICABILITY

The fcwf-SF cells of the present invention do not require fetal bovine serum or other protein additives derived from animals, and grow in a DFSP medium prepared by merely mixing an easily available, inexpensive and existing basal medium (Dulbecco's modified Eagle medium) and Nutrient Mixture (Ham's F-12)) with a decomposed product (soybean peptone) of plant-derived protein. When removal of the decomposed product of plant-derived proteins is also necessary, a culture medium for cells inoculated with a virus may be replaced by a medium not containing the same. Vaccine viruses or virus protein antigens used in various tests can thereby be produced inexpensively and safely. Particularly, kittens still retain antibodies transferred from queen, and should thus be inoculated frequently with vaccines in a short period in order to confer sufficient immunization on them. For example, the following circumstances can be mentioned. There is initial preventive inoculation against feline core viruses, that is, feline herpesvirus-1, feline calicivirus, and feline panleukopenia virus, as well as annual additional preventive inoculation of cats with high risk of infection. The safety of vaccines cannot be secured unless contamination with proteinous components other than the vaccine component is avoided as much as possible. Further, contamination of vaccines and pharmaceuticals with an unknown pathogen for "mad cow disease" attributable to prion that is problematic in recent years is an extremely anxious problem. Particularly, cats are highly sensitive to mad cow disease prion. The establishment of fcwf-SF cell strain by the animal-derived protein-free DFSP culture medium of the present invention provides an extremely useful means in development and production of pharmaceuticals using these cultured cells.

The invention claimed is:

1. An isolated cell strain, wherein the cell strain is a cell strain deposited under Accession No. FERM ABP-10594.

2. A method for producing a virus, comprising: infecting the cell strain of claim 1 with a virus, and culturing the infected cell strain to multiply the virus.

3. The method for producing a virus according to claim 2, wherein the medium in culturing the infected cell strain is an animal-derived protein-free medium containing a plurality of soybean-derived peptones in a 1:1 mixture of a Dulbecco's modified Eagle medium and Nutrient Mixture (Ham's F-12).

4. The method for producing a virus according to claim 2, wherein a suspension culture method is used in culturing the infected cell strain.

5. The method for producing a virus according to claim 2, wherein the virus is selected from the viral group consisting of Coronaviridae, Caliciviridae, Herpesviridae and Parvoviridae.

6. The method for producing a virus according to claim 2, wherein the virus is selected from feline calicivirus, feline enteric coronavirus, feline herpesvirus-1, feline parvovirus, canine parvovirus type 2, feline coronavirus, feline infectious peritonitis virus, canine coronavirus, canine respiratory coronavirus, transmissible gastroenteritis virus of swine, porcine epidemic diarrhea virus, and bovine coronavirus.

* * * * *